United States Patent [19]
Dorsey

[11] Patent Number: 5,950,320
[45] Date of Patent: Sep. 14, 1999

[54] MEDICO-SCIENTIFIC MEASURING DEVICE

[76] Inventor: Thomas R. Dorsey, 4364 Bonita Rd., Ste. 453, San Diego, Calif. 91902

[21] Appl. No.: 08/920,923

[22] Filed: Aug. 29, 1997

[51] Int. Cl.[6] .............................. A61B 1/00; G01B 11/28
[52] U.S. Cl. ................................................. 33/512; 33/1 N
[58] Field of Search ........................... 33/1 N, 511, 512, 33/534, 424, 494

[56] References Cited

U.S. PATENT DOCUMENTS

| | | | |
|---|---|---|---|
| D. 140,152 | 1/1945 | Aichele | D52/1 |
| D. 322,125 | 12/1991 | Dorsey | D24/140 |
| 1,961,500 | 6/1934 | Larson | 33/1 N |
| 2,011,282 | 8/1935 | Hochman | 33/1 N |
| 2,039,333 | 5/1936 | Musham | 33/1 N |
| 3,229,372 | 1/1966 | Quashnock et al. | 33/512 |
| 3,271,868 | 9/1966 | Kuntscher et al. | 33/143 |
| 3,812,842 | 5/1974 | Rodriguez | 128/2 A |
| 4,112,581 | 9/1978 | Hornsby | 33/534 |
| 4,201,226 | 5/1980 | Phillips | 128/774 |
| 4,279,259 | 7/1981 | Lee et al. | 128/774 |
| 4,490,921 | 1/1985 | Woods et al. | 33/476 |
| 4,630,375 | 12/1986 | Spolyar | 33/1 B |
| 5,033,200 | 7/1991 | Leung | 33/485 |
| 5,084,982 | 2/1992 | Feng | 33/534 |
| 5,361,506 | 11/1994 | Beeuwkes, III | 33/512 |

*Primary Examiner*—Bernard Roskoski
*Attorney, Agent, or Firm*—Frank G. Morkunas

[57] ABSTRACT

A medico-scientific measuring device of a substantially flat transparent material having a base edge and a half circle with an outer edge suitably marked for measuring angles; a horizontal plot line and a center point as a vertex adjacent to the base edge; a plurality of plot lines from the outer edge toward converging on the center point defining specific angles; a floating point indicia adjacent to, and in communication with, the center point; and a visible vertex gap axial from the floating point such that the horizontal plot lines and the converging plot lines are substantially interrupted to thereby facilitate a more accurate placement of the vertex and to provide a more accurate angle determination. The device may include in cooperating combination therewith a second measuring indicia for locating centerline and centerpoints on objects such as bones and the heads of bones; a third measuring indicia for accurately and quickly determining small distances (from about 1 mm to 10 mm); and a fourth measuring indicia such as a ruler for use in technical, scientific, and health-care related activities.

12 Claims, 3 Drawing Sheets

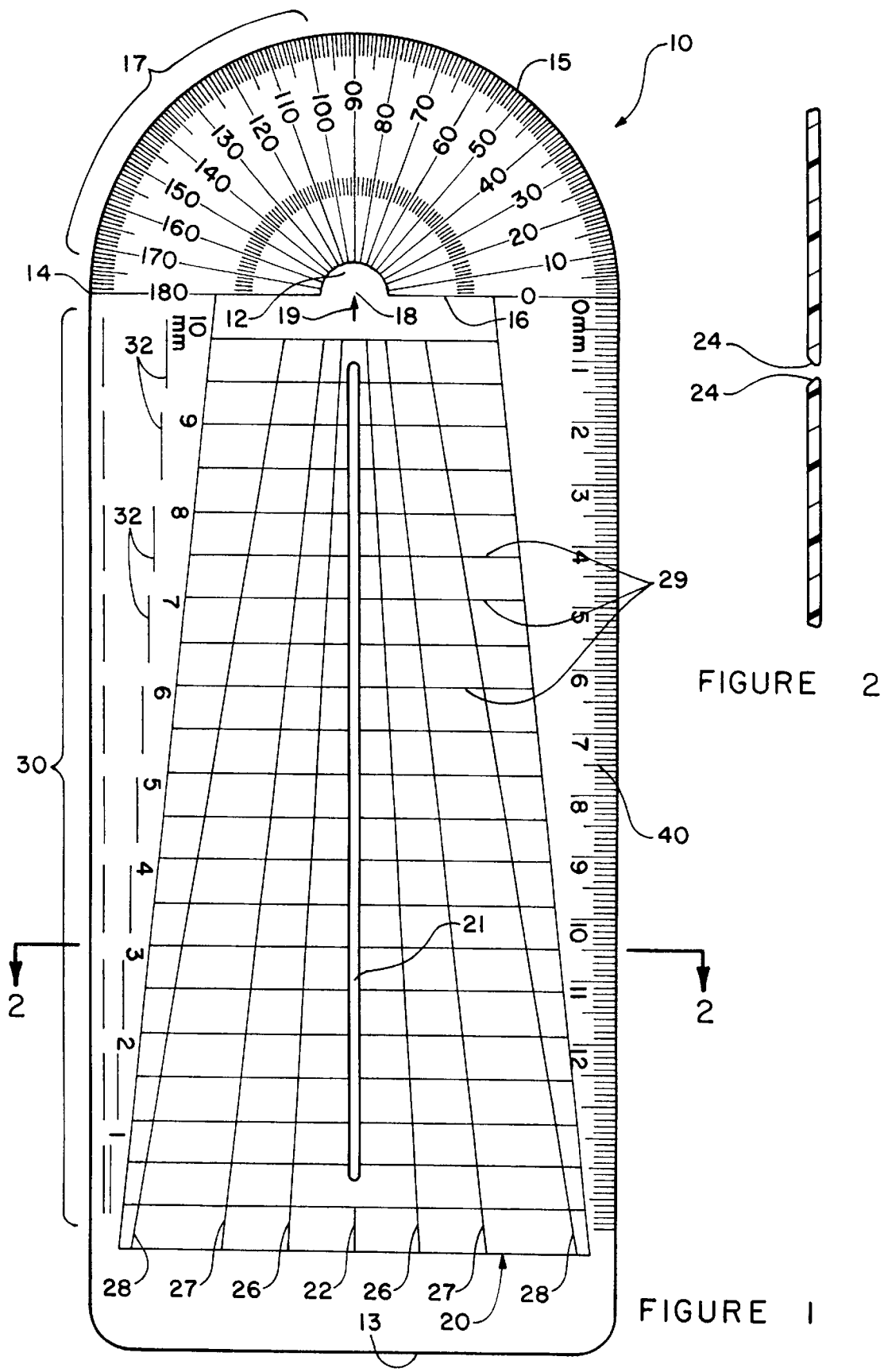

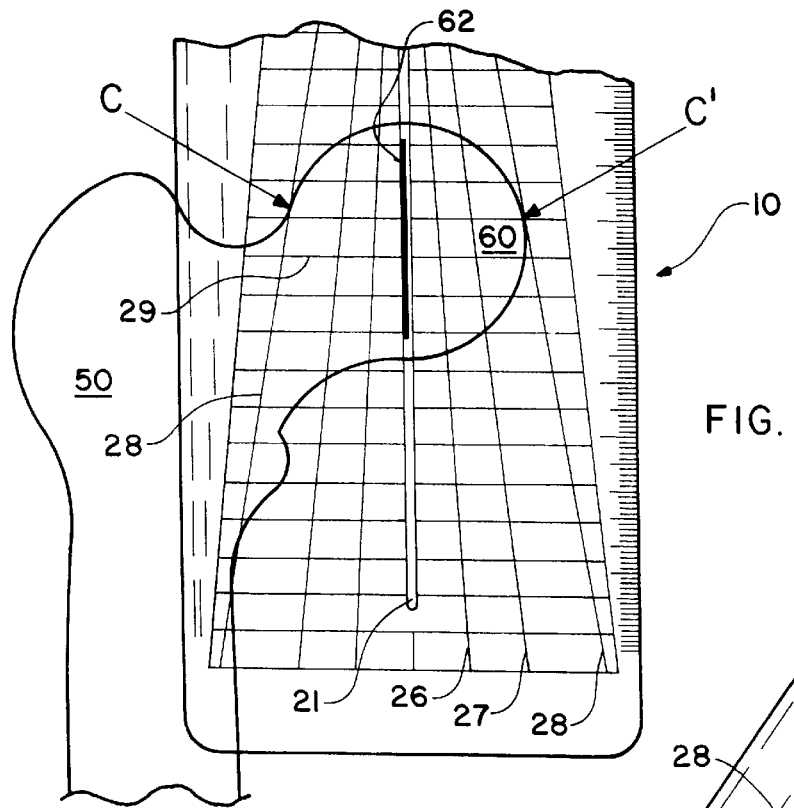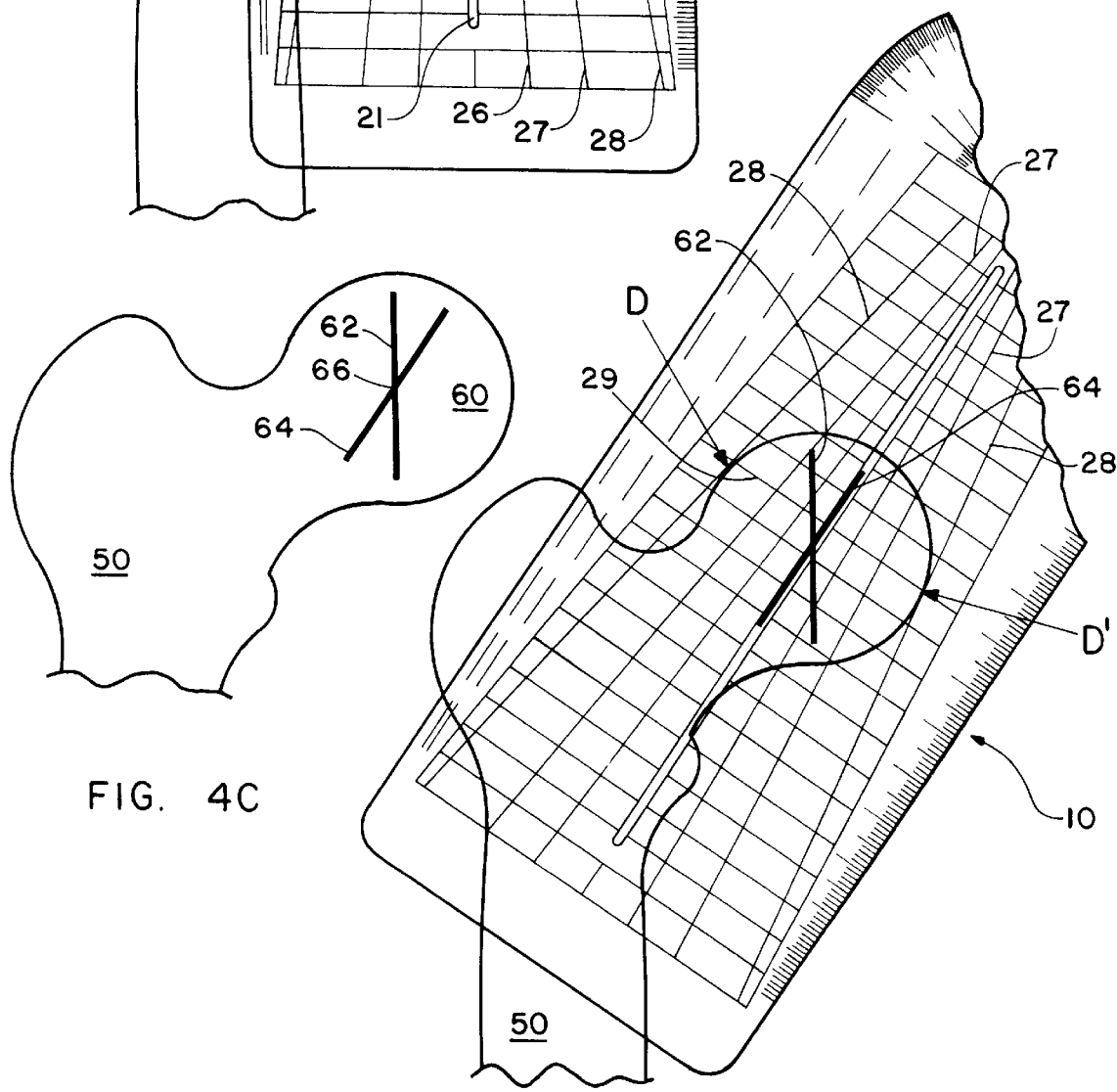
FIG. 4A
FIG. 4C
FIG. 4B

MEDICO-SCIENTIFIC MEASURING DEVICE

CROSS REFERENCES TO RELATED APPLICATIONS

Not Applicable

STATEMENT REGARDING FEDERALLY-SPONSORED RESEARCH OR DEVELOPMENT

Not Applicable

BACKGROUND OF THE INVENTION

This present invention relates to an improvement in medical and scientific measuring devices, and more particularly to a unique protractor incorporating a 'floating point' technology with a clearly defined vertex gap. The present invention, independent of, or in combination with, a plurality of other measuring devices including a centerline finder having a plurality of paired angled lines, each pair of a different color, and intersecting horizontal lines, of a color different from the color of any of the angled lines; and a small-distance discriminator for rapidly locating and measuring small distances at a glance. The device with its various measuring indicia, in combination, provide for a plurality of measurements associated with various technical fields of endeavor and, in the case of health care, for greater precision in measurement of angles, centers, and distances associated with, and necessary for, treatment and care.

In the medical field, and orthopedics in particular, the use of the floating point protractor permits for more accurate measurements and, concomitantly, better pre- and post-operative assessment, treatment, and care. In other technical fields, such as engineering, architecture, and machining, where precision is vital, the floating protractor also permits for greater precision angular accuracy which yields a better final product.

There are a multitude of scientific and technical-related combination devices suited for a variety of scientific and technical applications. U.S. Pat. No. 4,490,921 issued on Jan. 1, 1985, to Woods, discloses a combination drafting tool having a protractor, rulers, a centerline for the rulers, and a plurality of designs thereon. The vertex of the protractor is obscured with a continuous vertical and horizontal line therethrough.

U.S. Pat. No. 4,630,373 issued on Dec. 23, 1986, to Spolyar discloses an apparatus for gauging and determining spatial coordinates for a source of radiation which has a template-like gauge with a first, second, and third plurality of lines and a protractor-like device and a center of revolution (138) situated on the extension of a vertical line (114), said center being a clearly defined circle and without a substantial vertex gap or floating point indicia. In this device, the vertex of the protractor portion is not specifically indicated. Although there is a lack of convergence of the angular lines, the geometric vertex in not indicated. In this device, the 'zone of clearance' is quite small in comparison to the floating point configuration of the present invention. This zone makes using and reading quicker and easier. In addition, Spolyar's device refers to the center point as the 'center of revolution' to be used for obtaining a reading of the angle of occlusal plane (178). It cannot act independently of the composite device as an angular measuring device.

U.S. Pat. No. 5,033,200 issued on Jul. 23, 1991, to Leung discloses a scientific ruler having a plurality of lenses for use as a telescope, a ruler, an inclined plane adapted to refract sunlight into a rainbow spectrum, a comb, a thermometer, a plurality of mathematic signs, an undulate edge, and a protractor. This device, though comprising a variety of common implements, lacks the floating point technology of the present invention.

U.S. Pat. No. Des. 140,152 issued on Jan. 30, 1945, to Aichele discloses a drawing instrument having, among other features, a protractor. The center point of the protractor has converging horizontal lines, vertical lines, and one diagonal line thereat and is clearly without the floating point and vertex gap of the present invention.

U.S. Pat. No. Des. 322,125 issued on Dec. 3, 1991, to Dorsey (the applicant) discloses a unique design implement adapted to locate centerlines. This device has been found difficult to use, however, without utilizing differently colored lines throughout. Color is an important feature to the function of the present invention as it more easily maintains focus of use. When placing the device on an image which has clearly defined lines, the criss-crossing line pattern of the Dorsey device of the prior art inhibits proper focus. Color associated with the present invention fosters such focus, fosters alignment, and permits for greater discernibility and ease of operation. The present invention also incorporates a centerline and a beveled slot therethrough to facilitate placement of the device and marking.

A standard protractor has one or more converging plot lines meeting at a vertex. Such convergence obscures the vertex, however slightly in some cases, and renders it difficult to see and use for precision measurements. A true vertex is, therefore, more difficult to visualize with the concomitant result of a less-than-true measurement. True measurements are vital to engineering, architectural, scientific, and medical fields of endeavor. A true vertex will yield a true measurement and a better final result. Minute inaccuracies taint and skew results to the detriment of the study, endeavor, or treatment. In the medical field, when treating fractures for example, accuracy of angles—as well as the width of the fracture—is paramount. Slight deviations could affect the post-traumatic assessment and/or post-operative treatment regimen. Accuracy of such measurements leads to improved treatment and care.

None of the prior art devices, alone or in combination, discloses or the floating point technology and vertex gap of the present invention. None, alone or in combination, discloses or teaches a centerline finder structured with a beveled slot and different colored angled lines and different colored horizontal intersecting lines. None, alone or in combination, discloses or teaches a unique small distance discriminator for use in identifying and ascertaining minute separations. Only the present invention provides for the structure of the floating point with its vertex gap and their associated function; and, alone, or in combination with the centerline finder and/or the small distance discriminator provide for a unique functional combination suited for use in the medico-scientific fields of endeavor.

Accordingly, several objects and advantages of my invention are to:

a. facilitate the visualization of the vertex of an angle of interest when using a protractor in its normal sense or in combination with other medico-scientific measuring implements;

b. eliminate the need for guesswork and approximation in identifying a vertex point;

c. accurately and quickly identify and mark a centerline of a long object having symmetric, parallel, and non-parallel sides;

d. accurately and quickly identify minute distances; and e. provide, in a single device, a plurality of measurement devices which can be operated independently of one another or can interact with one another depending on the user's particular measurement needs.

The foregoing has outlined some of the more pertinent objects of the present invention. These objects should be construed to be merely illustrative of some of the more prominent features and applications of the intended invention. Many other beneficial results can be attained by applying the disclosed invention in a different manner or by modifying the invention within the scope of the disclosure. Accordingly, other objects and a fuller understanding of the invention may be had by referring to the summary of the invention and the detailed description of the preferred embodiment in addition to the scope of the invention defined by the claims taken in conjunction with the accompanying drawings.

BRIEF SUMMARY OF THE INVENTION

The above-noted problems, among others, are overcome by the present invention. Briefly stated, the present invention contemplates a medico-scientific measuring device of a substantially flat transparent material comprising a base edge and, outward therefrom, a half circle having an outer edge for measuring angles; a horizontal plot line adjacent to the base edge, the horizontal plot line having a center point as a vertex; a plurality of converging plot lines projecting radially from the outer edge toward, and in line with, the center point defining specific angles in relation to the center point; a floating point indicia adjacent to, and in communication with, the center point; and a visible vertex gap axial from the floating point such that the horizontal plot lines and the converging plot lines are substantially interrupted to thereby facilitate a more accurate placement of the vertex and to provide a more accurate angle determination.

The foregoing has outlined the more pertinent and important features of the present invention in order that the detailed description of the invention that follows may be better understood so the present contributions to the art may be more fully appreciated. Additional features of the present invention will be described hereinafter which form the subject of the claims. It should be appreciated by those skilled in the art that the conception and the disclosed specific embodiment may be readily utilized as a basis for modifying or designing other structures and methods for carrying out the same purposes of the present invention. It also should be realized by those skilled in the art that such equivalent constructions and methods do not depart from the spirit and scope of the inventions as set forth in the appended claims.

BRIEF DESCRIPTION OF THE DRAWINGS

For a fuller understanding of the nature and objects of the invention, reference should be had to the following detailed description taken in conjunction with the accompanying drawings in which:

FIG. 1 is a top plan view of the measuring device.

FIG. 2 is a cross section view of the measuring device taken along line 2—2 of FIG. 1.

FIGS. 4a through 4c are top plan views of the measuring device depicting its operation in locating the center point of the head of a large bone.

DETAILED DESCRIPTION OF THE INVENTION

Figure 3:
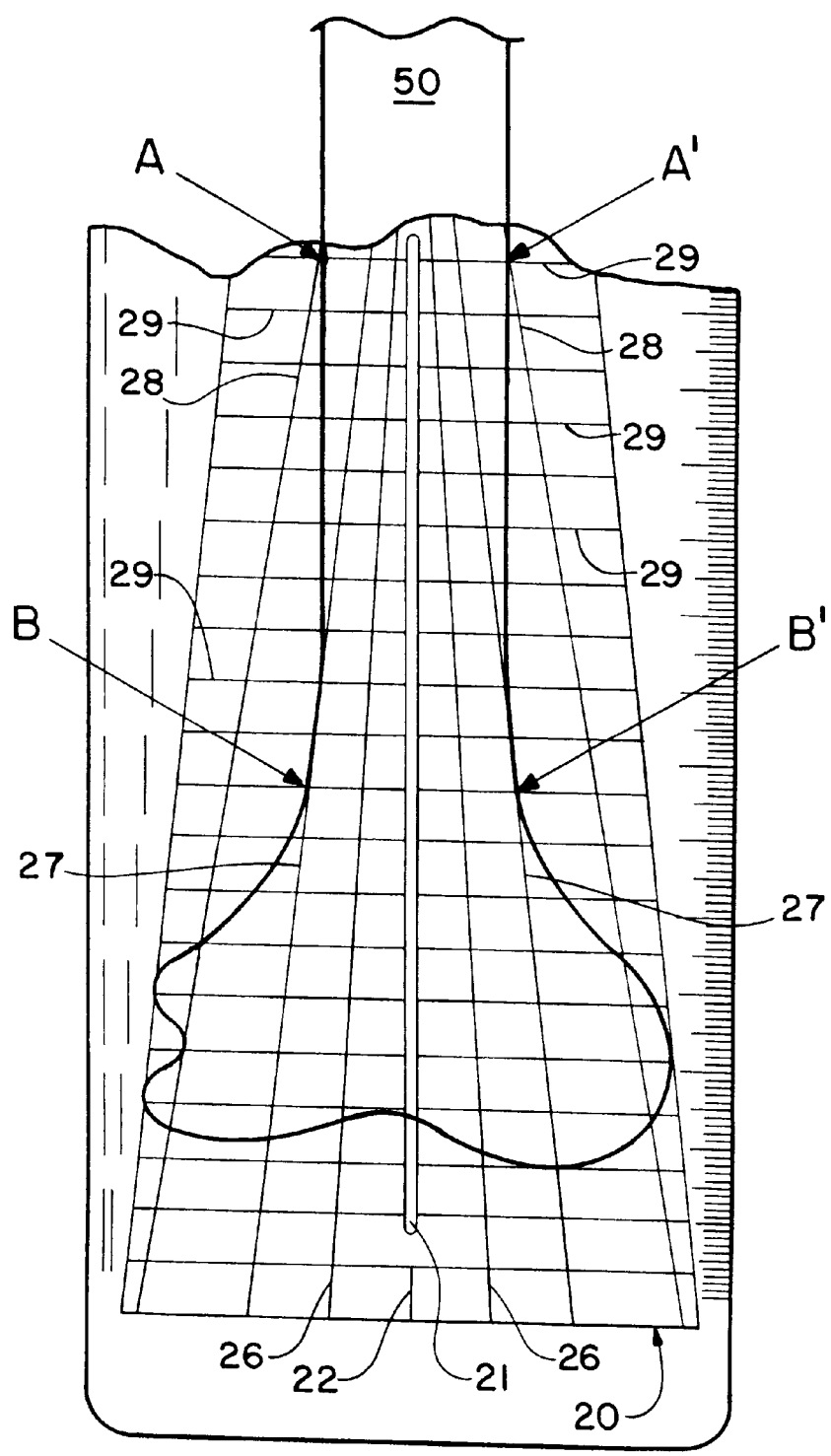
FIG. 3 is a top plan view of the measuring device, second indicia only, depicting its operation in locating the centerline of a bone.

Referring now to the drawings in detail and in particular to FIG. 1, reference character 10 generally designates a medico-scientific measuring device constructed in accordance with a preferred embodiment of the present invention. In its basic form, the medico-scientific measuring device 10 (a first measuring indicia 15) resembles a protractor device with a base edge 14 from which a half circle extends outward therefrom, horizontal base plot lines 16 adjacent to the base edge 14, and a plurality of converging and angled plot lines 17. The converging plot lines 17 comprise a plurality of angled lines converging radially from the outer edge of the half circle of the medico-scientific measuring device 10 toward and ending at a center point, or the vertex 18. An indicia, such as an arrow 19 or a pointer, clearly marks the vertex 18. All the converging plot lines 17 and the horizontal plot lines 16 are substantially interrupted and do not extend to the vertex 18 and its marking indicia 19. A clear area is defined hereat and is referred to as the vertex gap 12. It is about this vertex gap 12 that the vertex 18 and its indicia 19 establish the structure and function of what is referred to as the floating point.

By eliminating the structural convergence of more than one line from the outer periphery to the vertex, as applied to and found on standard protractors, the floating point 19 of the first measuring indicia 15 facilitates the visualization of the vertex 18 of any angle of interest for a user. As so structured with the floating point 19 and the vertex gap 12 any angle of interest easily can be exquisitely, rapidly, and accurately visualized and annotated. Such visualization is enhanced when the distance from the vertex 18 to the outer periphery of the vertex gap 12 ranges from about 5–25 length % of the total distance from the vertex 18 to the outer edge of the half circle. It has been found that even better visualization is achieved when this distance ranges from about 10–15 length %. The best achieved visualization, however, lies at about 13 length %.

Another embodiment of the medico-scientific measuring device 10 includes a second technical measuring indicia 20 adapted to discerning centerlines of elongated objects having regular or irregular sides, such as bones, and for identifying and locating exact centers for the heads of bones. Used in combination with the first measuring indicia 15 for accurate angles, this medico-scientific measuring device becomes an indispensable device for, and by way of example only and not limitation, the orthopedic practitioner.

An example here includes the measurement of abnormal angulation at a bone fracture site. The central slotted portion of the second measuring indicia 20 would be used to identify and mark the centerline of the respective bones. The first measuring indicia 15 would then quickly and easily be used to clearly ascertain the degree of angulation of those bones. Determining the degree of angulation of a fracture, among other factors, is an important factor in making all treatment-related decisions; i.e., whether or not surgery is necessary. Determining the degree of angulation, and whether or not treatment has restored normal alignment, is equally important in all post-treatment decision-making.

The second measuring indicia 20 is attached to the fist measuring indicia 15 at the base edge of the first measuring indicia 15. A substantially centered slot 21 runs from the bottom of the second measuring indicia upward to substantial adjacency of the floating point 19. As shown in FIG. 2, the slot is substantially beveled. The second measuring indicia has a lateral center 22 which is in substantially direct alignment with the vertex 18 of the first measuring indicia. The second measuring indicia also has a plurality of paired angled lines 26, 27, and 28 beginning at the top of the second measuring indicia running downward and outwardly angled from the slot 21 to the bottom of the second measuring indicia.

Each set of paired and angled lines is equally spaced from the slot 21. Each set of paired and angled lines also has its own distinctive color apart from the color of any other such set. Differences in colors is important for discriminating the sets from one another when performing a measurement function. Intersecting each pair of angled lines are a plurality of horizontal lines 29. These horizontal intersecting lines 29 are substantially perpendicular to the slot 21 and are of a color different from the colors of the paired and angled lines 26, 27, and 28. Color is an important feature of the second measuring indicia and is of an equal importance to its proper function.

To find a centerline of a bone image on a radiograph, for example, four points on the edge of the bone must be identified by two different horizontal intersecting lines 29 of the second measuring indicia 20. The first two points must be on one horizontal intersecting line 29 at which one pair of angled lines (either 26, 27, or 28) intersect the specific horizontal line and also meet the edges of the bone. The second two points must be on another horizontal intersecting line 29 at which another pair of angled lines intersect that other horizontal line and also meet the edges of the bone. After these four points are found, a suitable marking implement is inserted into the slot 21 and a line is drawn therethrough on the image. This is the centerline of the object.

FIG. 3 shows this operation. For clarity, FIG. 3 shows only the second measuring indicia without any other measuring indicia distracting this illustration. The second measuring indicia 20 is placed on an image of a bone 50 as captured by a radiograph. Points A and A' show where paired angled lines 28 intersect one of the plurality of horizontal lines 29 and touch thereat the opposite edges of the bone 50. With points A and A' held, the second two points, B and B', are shown where the second pair of paired angled lines 27 intersect another of the plurality of horizontal lines 29 and touch thereat the opposite edges of the bone 50 at a different location. With the medico-scientific measuring device held in place, a centerline is drawn through slot 21. The different colors of the paired angled lines make it easy to focus on the points of interest of the object to be measured and to maintain focus on the respective horizontal intersecting line in relation to the edges of the object to be measured.

FIGS. 4a through 4c illustrate how to find the center of the head of a bone, such as the femoral head 60 for example. To do so, the second measuring indicia 20 is placed where the outer edges of the femoral head meet any matched pair of angled lines (either 26, 27, or 28) on the same horizontal intersecting line 29. In FIG. 4a, the outer edges of the femoral head meet angled lines 28 and horizontal intersecting lines 29 at points labeled C and C'. A first mark 62 is made through the image of the femoral head 60 by placing a marking implement in the slot 21 and drawing the mark. The second measuring indicia 20 is then rotated in either direction approximately between 20 to 90 degrees and, following the same process, a second mark 64 is drawn on the image. This is shown in FIG. 4b with the meeting points labeled as D and D'. FIG. 4c reveals the 'X' so formed. The center 66 of the femoral head is where the two lines of the 'X' mark intersect.

Use of the first measuring indicia 10 in combination with the second measuring indicia 20 permits, with one device, a practitioner to easily, quickly, and clearly identify bone centers, bone head centers, and, as necessary, ascertain relative angles associated with bone structures. Identification of bone head centers, particularly those of the head of the femur, are crucial in pre-operative diagnosis and assessments in total joint surgery as well as for pediatric orthopedic surgery. Following the identification of femoral head centers, the second measuring indicia can then be brought into place to identify the centerline of the femoral neck; also a common measurement made in anticipation of such surgeries. This enables the practitioner to more accurately assess the situation and pursue the best course of treatment to include, or not include, surgery.

Similar measurements are vital post-operatively to assess the effectiveness of the treatment selected and what, if any, additional procedures may be indicated.

Another embodiment of the medico-scientific measuring device includes a third measuring indicia 30 adjacent to the base edge 14 and the second measuring indicia 20. The third measuring indicia 30 comprises a plurality of small distance discriminators 32. Each such small distance discriminator 32 consists of one pair of substantially parallel lines with no intervening lines therein between. The distance between each such pair is different than any other such pair. A value indicia adjacent to each such pair communicates the distance between each line in the pair. In this embodiment, there are ten pairs of small distance discriminators reflecting a value from 1 to 10. The number value in this example represents the distance, in millimeters, between the pairs. Any type of unit of measure may be used.

It has been found that the vertical distance of the lines is important to function. Lines too short or too long make viewing the image and using the device more difficult. Vertical distances ranging from about 0.5 cm to about 2.0 cm have proved satisfactory. The ideal vertical distance, however, is about 1.0 cm.

This third measuring indicia 30 is particularly useful when dealing with small gaps or distances reflected by, for example and not by way of limitation, an image of a bone cast on a radiograph which discloses a fracture. The fracture lines vary in length and width. Minute distances are difficult to discern by using a conventional measuring device such as a ruler because of the plurality of incremental indicia thereon which tend to obscure the exact locations of the end sites to be measured. Precision in many cases is paramount for treatment and care. The small distance discriminator easily captures the distances of such fractures quickly and accurately.

The utility of the third measuring indicia 30 lies in the fact that it allows rapid visual determination of distances. The quickness and accuracy of use minimizes eye strain, virtually ensures a precision measurement, and decreases the time required to complete the measurement by approximately 60%. Before treating fractures it is critical to view them on a radiograph and to accurately measure their location, their width, and their angulation—angulation in relation to the fracture itself, in relation to the bone surfaces, and in relation to the center of the bone. Each of the measuring indicia described above, alone, or in cooperating combination provide for accurate angle measurements (first indicia), for locating centerlines and center points for the heads of bones (second indicia), and accurate length and width measurements (third indicia). These indicia, alone or in cooperating combination provide speed and accuracy vital to proper treatment and care.

Another embodiment of this invention has a fourth measuring indicia 40 adjacent to the base edge 14. This is a standard-type ruler, using any type of unit of measure, to fill in miscellaneous measurement functions associated with treatment and care which cannot adequately be fulfilled by any of the other measuring indicia on the medico-scientific measuring device.

The present disclosure includes that contained in the present claims as well as that of the foregoing description. Although this invention has been described in its preferred forms with a certain degree of particularity, it is understood that the present disclosure of the preferred forms has been made only by way of example and numerous changes in the details of construction and combination and arrangement of parts may be resorted to without departing from the spirit and scope of the invention. Accordingly, the scope of the invention should be determined not by the embodiment[s] illustrated, but by the appended claims and their legal equivalents.

The invention claimed is:

1. A medico-scientific measuring device of a substantially flat transparent material comprising:
   a. a base edge, said base edge defining a half circle outward therefrom, said half circle having an outer edge for measuring angles;
   b. a horizontal plot line adjacent to said base edge, said horizontal plot line having a center point;
   c. a plurality of converging plot lines projecting radially inward from the outer edge of said half circle toward, and in line with, said center point thereby defining specific angles in relation to said horizontal plot line;
   d. a floating point indicia having a tip and structured adjacent to, and in communication with, said center point such that said tip defines a vertex for all said converging plot lines with said horizontal plot line;
   e. a visible vertex gap axial from said floating point such that said horizontal plot line and said converging plot lines are substantially interrupted at a clearly defined outer periphery of said vertex gap to facilitate a more accurate placement of the device and to provide a more accurate angle determination from said outer edge to said vertex gap; and
   f. a second measuring indicia for locating center lines, said second measuring indicia adjacent to said base edge and further comprising a lateral center at one end of said second measuring indicia, said lateral center in line with said tip of said floating point and substantially perpendicular to said horizontal plot line, a slot communicating through said second measuring indicia, said slot being adjacent to said lateral center and said floating point, at least one pair of angled lines having a line on either side of, and equidistant from, said slot, said at least one pair of angled lines bearing a first distinctive color, and a plurality of horizontal intersecting lines substantially perpendicular to said slot, intersecting said at least one pair of angled lines, and bearing a second distinctive color.

2. The device as defined in claim 1 wherein said second measuring indicia further comprises a plurality of additional paired angled lines, each said additional paired angled lines bearing a different distinctive color from said at least one pair of angled lines, from other said additional paired angled lines, and from said plurality of horizontal intersecting lines, each line of each pair of said additional paired angled lines being on either side of, and equidistant from, said slot.

3. The device as defined in claim 1 wherein said slot has beveled side walls.

4. The device as defined in claim 1 further having a third measuring indica on said transparent material for discriminating small distances, said second measuring indicia adjacent to said base edge and comprising:
   a. a plurality of paired parallel lines of varying spaced distances; and
   b. a value indicia adjacent to each said paired parallel lines, said value indicia communicating to a user of said device the distance between each parallel line of each pair of said paired parallel lines.

5. The device as defined in claim 1 further having a fourth measuring indicia for incrementally measuring distances, said fourth measuring indicia adjacent to said base edge and comprising a plurality of uniformly spaced parallel lines.

6. The device as defined in claim 5 wherein said plurality of uniformly spaced parallel lines further have sequentially incremented value indicia.

7. A medico-scientific measuring device of a substantially flat transparent material comprising:
   a. a base edge, said base edge defining a half circle outward therefrom, said half circle having an outer edge for measuring angles;
   b. a horizontal plot line adjacent to said base edge, said horizontal plot line having a center point;
   c. a plurality of converging plot lines projecting radially inward from the outer edge of said half circle toward, and in line with, said center point thereby defining specific angles in relation to said horizontal plot line;
   d. a floating point indicia having a tip and structured adjacent to, and in communication with, said center point such that said tip defines a vertex for all said converging plot lines with said horizontal plot line;

e. a visible vertex gap axial from said floating point such that said horizontal plot line and said converging plot lines are substantially interrupted at an outer periphery of said vertex gap to facilitate a more accurate placement of the device and to provide a more accurate angle determination; and f. a measuring indica for discriminating small distances, said measuring indicia for discriminating small distances being adjacent to said base edge and comprising a plurality of paired parallel lines of varying spaced distances on said transparent material and a value indicia adjacent to each said paired parallel lines, said value indicia communicating to a user of said device the distance between each parallel line of each pair of said paired parallel lines.

8. The device as defined in claim 7 further having a measuring indicia for locating center lines, said measuring indicia for locating center lines being adjacent to said base edge and comprising:

a. a lateral center at one end of said measuring indicia for locating center lines, said lateral center in line with said tip of said floating point and substantially perpendicular to said horizontal plot line;

b. a slot communicating through said measuring indicia for locating center lines, said slot being adjacent to said lateral center and said floating point;

c. at least one pair of angled lines having a line on either side of, and equidistant from, said slot, said at least one pair of angled lines bearing a first distinctive color; and d. a plurality of horizontal intersecting lines substantially perpendicular to said slot, intersecting said at least one pair of angled lines, and bearing a second distinctive color.

9. The device as defined in claim 8 wherein said measuring indicia for locating center lines further comprises a plurality of additional paired angled lines, each said additional paired angled lines bearing a different distinctive color from said at least one pair of angled lines, from other said additional paired angled lines, and from said plurality of horizontal intersecting lines, each line of each pair of said additional paired angled lines being on either side of, and equidistant from, said slot.

10. The device as defined in claim 8 wherein said slot has beveled side walls.

11. The device as defined in claim 7 further having a measuring indicia for incrementally measuring distances, said measuring indicia for incrementally measuring distances being adjacent to said base edge and comprising a plurality of uniformly spaced parallel lines.

12. The device as defined in claim 7 wherein said plurality of uniformly spaced parallel lines further have sequentially incremented value indicia.

* * * * *